United States Patent
Choi

(10) Patent No.: US 12,191,037 B2
(45) Date of Patent: Jan. 7, 2025

(54) MEDICAL MACHINE LEARNING SYSTEM

(71) Applicant: VISUAL TERMINOLOGY INC., Busan (KR)

(72) Inventor: Byung Kwon Choi, Busan (KR)

(73) Assignee: VISUAL TERMINOLOGY INC., Busan (KR)

( * ) Notice: Subject to any disclaimer, the term of this patent is extended or adjusted under 35 U.S.C. 154(b) by 482 days.

(21) Appl. No.: 17/607,234

(22) PCT Filed: Apr. 6, 2020

(86) PCT No.: PCT/KR2020/004611
§ 371 (c)(1),
(2) Date: Apr. 13, 2022

(87) PCT Pub. No.: WO2020/231007
PCT Pub. Date: Nov. 19, 2020

(65) Prior Publication Data
US 2022/0246301 A1  Aug. 4, 2022

(30) Foreign Application Priority Data
May 13, 2019  (KR) .......... 10-2019-0055698

(51) Int. Cl.
*G16H 50/20* (2018.01)
*G06N 20/00* (2019.01)

(52) U.S. Cl.
CPC .......... *G16H 50/20* (2018.01); *G06N 20/00* (2019.01)

(58) Field of Classification Search
CPC ........ G16H 50/20; G16H 30/40; G16H 50/50; G16H 50/70; G16H 15/00; G16H 50/80;
(Continued)

(56) References Cited

U.S. PATENT DOCUMENTS

| 10,037,820 B2* | 7/2018 | Wong ...................... G16H 50/50 |
| 2015/0134361 A1* | 5/2015 | Molenda ................ G16H 15/00 705/3 |
| 2017/0177795 A1* | 6/2017 | Mabotuwana ......... A61B 6/037 |

FOREIGN PATENT DOCUMENTS

| KR | 10-2015-0108701 A | 9/2015 |
| KR | 10-2017-0061222 A | 6/2017 |
| KR | 10-2018-0040287 | * 4/2018 |
| KR | 10-2018-0040287 A | 4/2018 |
| KR | 10-1857624 B1 | 5/2018 |

(Continued)

OTHER PUBLICATIONS

Ruan et al., "Pictorial Visualization Of EMR Summary Interface And Medical Information Extraction Of Clinical Notes", 2018 IEEE International Conference On Computational Intelligence And Virtual Environments For Measurement System And Applications (CIVEMSA), Jun. 2018, pp. 1-6, IEEE (Year: 2018).*

(Continued)

*Primary Examiner* — Joy Chng
(74) *Attorney, Agent, or Firm* — Paratus Law Group, PLLC

(57) ABSTRACT

Disclosed is a medical equipment learning system which includes: a data extraction module configured to collect and then extract text-type data from medical data; a visualization module configured to generate image-type data as visualization data by using the text-type data extracted by the data extraction module; a pre-processing module configured to generate an input data set to execute equipment learning based on the visualization data; a learning module configured to execute equipment learning in the input data set generated by the pre-processing module; a prediction module configured to predict a disease when new image-type data is input based on the result learned in the learning module; and a storage module provided to store and check data of each module.

12 Claims, 16 Drawing Sheets

(58) Field of Classification Search
CPC ........ G16H 70/00; G06N 20/00; G06N 3/045; G06N 3/08
USPC ...................................................... 705/2–3
See application file for complete search history.

(56) References Cited

FOREIGN PATENT DOCUMENTS

| KR | 10-1884609 B1 | 8/2018 |
|---|---|---|
| KR | 10-2018-0098869 A | 9/2018 |

OTHER PUBLICATIONS

De Ridder et al., "A web-based medical multimedia visualization interface for personal health records", Proceedings of the 26th IEEE International Symposium On Computer-Based Medical Systems, Jun. 2013, pp. 191-196, IEEE (Year: 2013).*

International Search Report for PCT/KR2020/004611 mailed Oct. 29, 2020 from Korean Intellectual Property Office.

Korean Office Action for related KR Application No. 10-2019-0055698 mailed Jan. 13, 2021 from Korean Intellectual Property Office.

Wei Ruan et al., "Pictorial visualization of EMR summary interface and medical information extraction of clinical notes", 2018 IEEE International Conference on Computational Intelligence and Virtual Environments for Measurement System and Applications (CIVEMSA), Jun. 2018, pp. 1-6, IEEE.

Michael De Ridder et al., "A web-based medical multimedia visualisation interface for personal health records", Proceedings of the 26th IEEE International Symposium on Computer-Based Medical Systems, Jun. 2013, pp. 191-196, IEEE.

* cited by examiner 221  222  223  224

(a)  (b)  (c)

```
<Diagnosis>
  <item>
    Hepatitis
  </item>
  <item>
    Stroke
  </item>
</Diagnosis>
```

MEDICAL MACHINE LEARNING SYSTEM

CROSS-REFERENCE TO PRIOR APPLICATIONS

This application is a National Stage patent application of PCT International Patent Application No. PCT/KR2020/004611 (filed on Apr. 6, 2020) under 35 U.S.C. § 371, which claims priority to Korean Patent Application No. 10-2019-0055698 (filed on May 13, 2019), which are all hereby incorporated by reference in their entirety.

BACKGROUND

The present invention relates to a medical equipment learning system, and more particularly, to a medical artificial intelligence (AI) learning system provided to be used for medical AI learning by converting medical data expressed by texts into image data and using the converted image data.

As existing paper charts are evolved and changed into electronic medical record systems, types of medical data that can be recycled have also increased rapidly. The era is coming in which more lifelogs including various biological signals, etc. are stored more rapidly by utilizing a lot of sensor data derived from the Internet of Things.

In addition, as the trend of medical services is changing from treatment to prevention and health management, researches of artificial intelligence (AI) using medical data are developing. Through this, occurrence of diseases to be suffered by patients, a life expectancy, side effects of treatment, etc. are predicted or personalized services have also been rapidly evolved according to the prediction.

On the other hand, medical data includes a lot of data such as imaging test results, medical records, surgical records, nursing records, and blood tests, and in terms of utilization, medical image data was frequently used in the early stage of AI development. The reason is that the imaged data cannot be extracted directly from the medical image, does not require much cooperation from a medical person, and has basic data constituted in an array of numbers, and thus it is suitable for learning. In addition, the image-type data can make the length of the data constant and thus has made much progress. Recently, image-based AI that diagnoses lung cancer or reads bone age from a lung CT has been introduced.

On the other hand, text-type data that is not an image in the medical data has not made much progress, and the reason is that it is difficult to normalize the data and to convert the data into structured data because the uncertainty of the meaning of the text is large and the length of the data is not easily matched.

A representative method of methods of learning text-type data known so far is a method of using natural language processing. This is a method of equipment learning with a vector that substitutes words with numbers, and equipment learning for language is performed by using techniques such as Bag of words, Text Frequency-Inverse Document Frequency (TF-IDF), skip-gram, and word2vec.

A second method is a method of standardizing various medical data and designating the standardized medical data as a standard data model with various additional information. For example, the method is a method of specifying a data structure format such as an abdominal pain model, a headache model, and an appendicitis model, defining items of the model, and then structuring the defined items. However, the disadvantage of this method is that a problem may occur when using a data model having a different structure for each hospital or when there is data of missing items.

A third method is a method of using a standard terminology system. However, this method has disadvantages of having a problem of expression, making a lot of extra efforts in coding, and being not able to include uncoded data. In addition, language materials may be difficult to show the variation of a patient's condition over time, and particularly, in such a case where disease is improved or the disease is cured repeatedly, the language materials may be difficult to process a complicated temporal trend with text-based data.

SUMMARY

The present invention is derived to solve these problems and an object of the present invention is to provide a medical artificial intelligence (AI) learning system capable of avoiding disadvantages of existing text-type data and improving performance of AI by converting medical information expressed in texts into images and using the converted images for AI learning.

The technical objects of the present invention are not limited to the aforementioned technical objects, and other technical objects, which are not mentioned above, will be apparently appreciated by a person having ordinary skill in the art from the following description.

A medical equipment learning system according to the present invention comprises:
  a data extraction module (100) configured to collect and then extract text-type data (120) from medical data (110);
  a visualization module (200) configured to generate image-type data (210) as visualization data by using the text-type data (120) extracted by the data extraction module (100);
  a pre-processing module (300) configured to generate an input data set (310) to execute equipment learning based on the visualization data;
  a learning module (400) configured to execute equipment learning in the input data set (310) generated by the pre-processing module (300);
  a prediction module (500) configured to predict a disease when new image-type data (210) is input based on the result learned in the learning module (400); and
  a storage module (600) provided to store and check data of each module.

The visualization data generated by the visualization module (200) may be a predetermined 2D or 3D model.

The data extraction module (100)
  may collect the medical data (110) by receiving materials from any one or more of a portable file, a hospital, a cloud server, and a personal device.

The visualization module (200)
  may change any one or more of colors, brightness or transparency, patterns, and textures of the visualization data according to the name of a disease, the severity of the disease, the chronicity, the degree of malignancy, various test results, functional test results, and data results extracted from an equipment.

The pre-processing module (300)
  may generate the input data set (310) by pre-processing various types of image-type data (210) having various formats.

By the technical solution, according to the present invention, it is possible to provide a medical AI learning system capable of avoiding disadvantages of existing text-type data (120) and improving performance of AI by converting text-type medical information into images and then using those images for equipment learning.

Further, it is possible to normalize text-type data which have different lengths while having ambiguous meanings.

Further, it is possible to provide an equipment learning data set (310) having a richer meaning by converting text-type data into image-type data.

Further, it is possible to implement a medical AI system capable of predicting precise and accurate data.

DETAILED DESCRIPTION

Terms used in the present specification will be described in brief and the present invention will be described in detail.

Terms used in the present invention adopt general terms which are currently widely used as possible by considering functions in the present invention, but the terms may vary depending on an intention of those skilled in the art, a precedent, emergence of new technology, etc. Accordingly, the terms used in the present invention should be defined based on not just a name of the term but a meaning of the term and contents throughout the present invention.

Throughout the specification, when any part "comprises" any component, the part may further include other components instead of excluding other components unless specifically stated otherwise.

An embodiment of the present invention will be described more fully hereinafter with reference to the accompanying drawings so as to be easily implemented by those skilled in the art. However, the present invention may be embodied in many different forms and is not limited to embodiments described herein.

Specific matters including problems to be solved for the present invention, solutions of the problems, and the effects of the invention for the present invention are included in embodiments and drawings to be described below. Advantages and features of the present invention, and methods for accomplishing the same will be more clearly understood from embodiments described in detail below with reference to the accompanying drawings.

Hereinafter, the present invention will be described in more detail with reference to the accompanying drawings.

Figure 1:
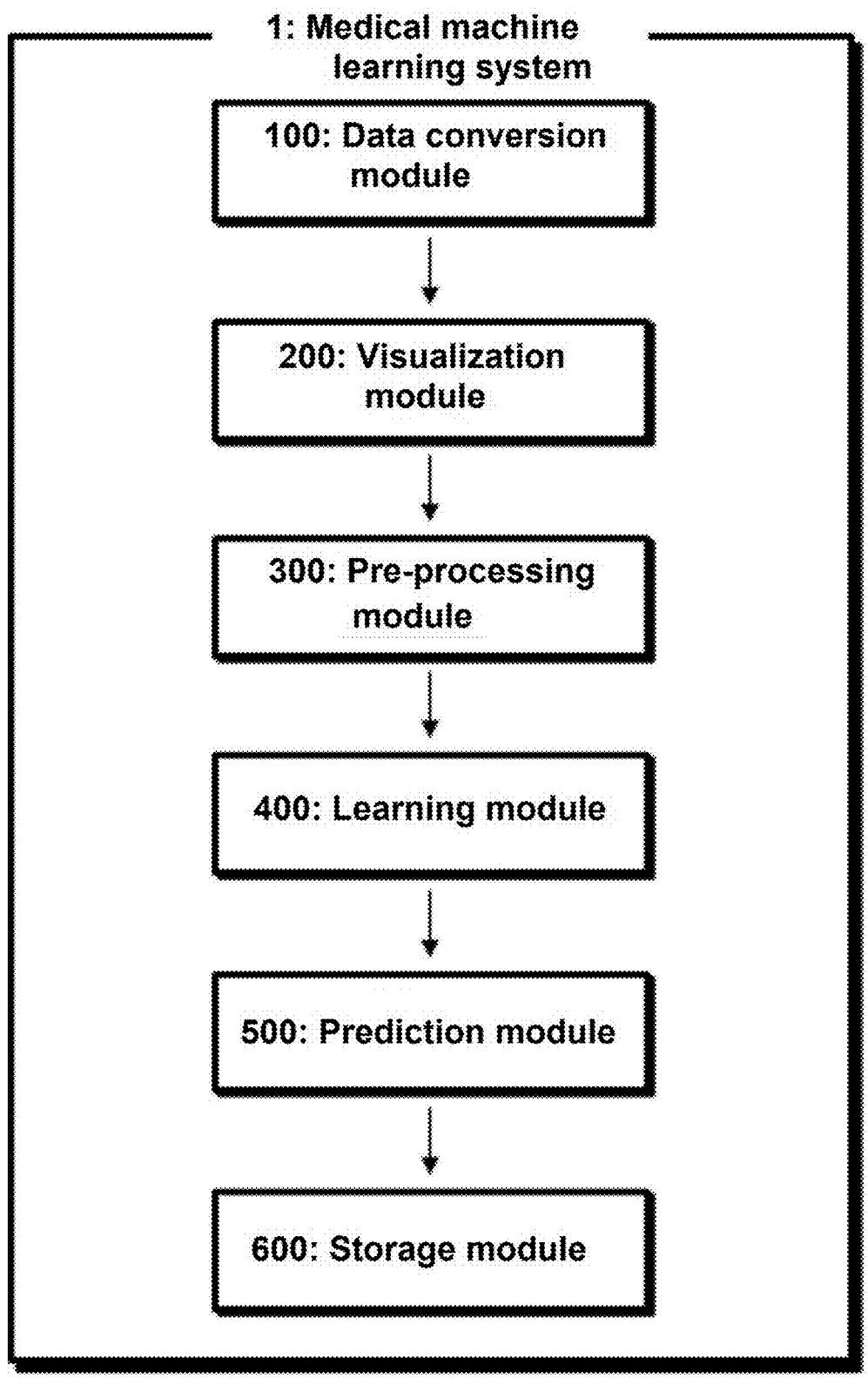
FIG. 1 is a configuration diagram illustrating a configuration of a medical equipment learning system of the present invention.

As illustrated in FIG. 1, a medical equipment learning system of the present invention is largely configured by including a data extraction module 100, a visualization module 200, a pre-processing module 300, a learning module 400, a prediction module 500, and a storage module 600.

First, the data extraction module 100 serves to extract necessary information from medical data 110 to generate text-type data 120. A subject to be extracted may be a clinical document received via USB or e-mail, as well as a hospital, or electronic medical record system materials stored in the hospital. These materials may be stored in document forms or stored in a database as materials. When a patient visits as an outpatient or is hospitalized several times, the medical materials may be prepared according to the patient, and thus the data extraction module 100 serves to extract the data in a required form. Further, the data extraction module 100 may extract the data from materials received from other hospitals or even from materials stored in a server outside the hospital, materials stored in a personal device, or materials received from various medical devices.

The text-type data 120 means text-type data included in the medical data 110, such as disease names or diagnosis names, symptoms, blood test results, reading papers, surgical names, nursing records, and nursing measures, as data acquired from the medical data 110 represented as clinical records, electronic medical records, progress recodes, discharge summaries, medical terminologies, or other many text types or number types.

The text-type data 120 is not limited to a diagnosis name, and the text-type data 120 may include data defined in anatomical sites, procedure names, measured blood pressure values, and the activity of a patient of a massage medical person or a medical assistant, or various text-type materials indicating patient's conditions such as "serious", "light", "large", and "small". For example, the text-type data 120 may be Korean or English characters such as "fatty liver", "ankle pain", and "heart failure", or standardized data or medical term codes such as "K76.0", "61515", "N05", and "M51.0", which are numbers or combinations of characters and numbers. The standardized medical term code refers to a range in which medical concepts are presented in SNOMED-CT, ICD-9, ICD-10, ICD-11, LOINC, CPT, ATC, RxNorm, ICNP, NMDS, and the like. In addition, a test result of a hemoglobin level of 10.3 gram/deciliter may be data expressed by numbers.

Figure 16:
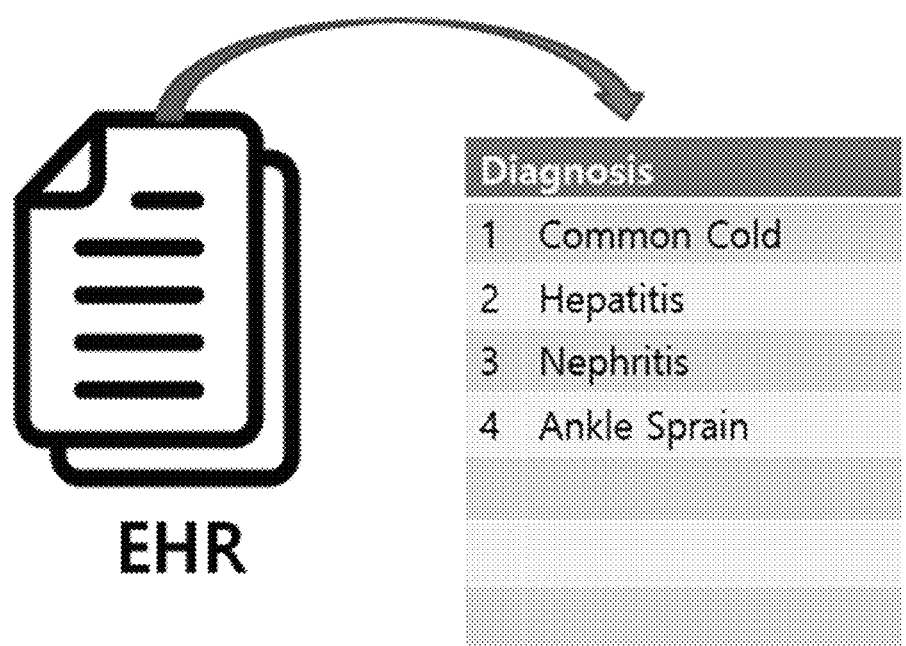
FIG. 16 is an embodiment illustrating a method of extracting data by the data extraction module (100) when the text-type data (120) for generating the image-type data (210) is stored in the medical data (110) as a separate item.

FIG. 16 is an embodiment illustrating that data required for extracting the text-type data 120, such as a medical record document, are stored in the electronic medical record system as separate items. In this case, the text-type data 120 may be extracted by accessing the database and reading only required items. In addition, in the data stored in the form of a document, as illustrated in FIG. 17, data in the form of JSON or XML may be classified for each diagnosis name or each symptom, and at this time, the required items may be read and taken.

Figures 17, 18:
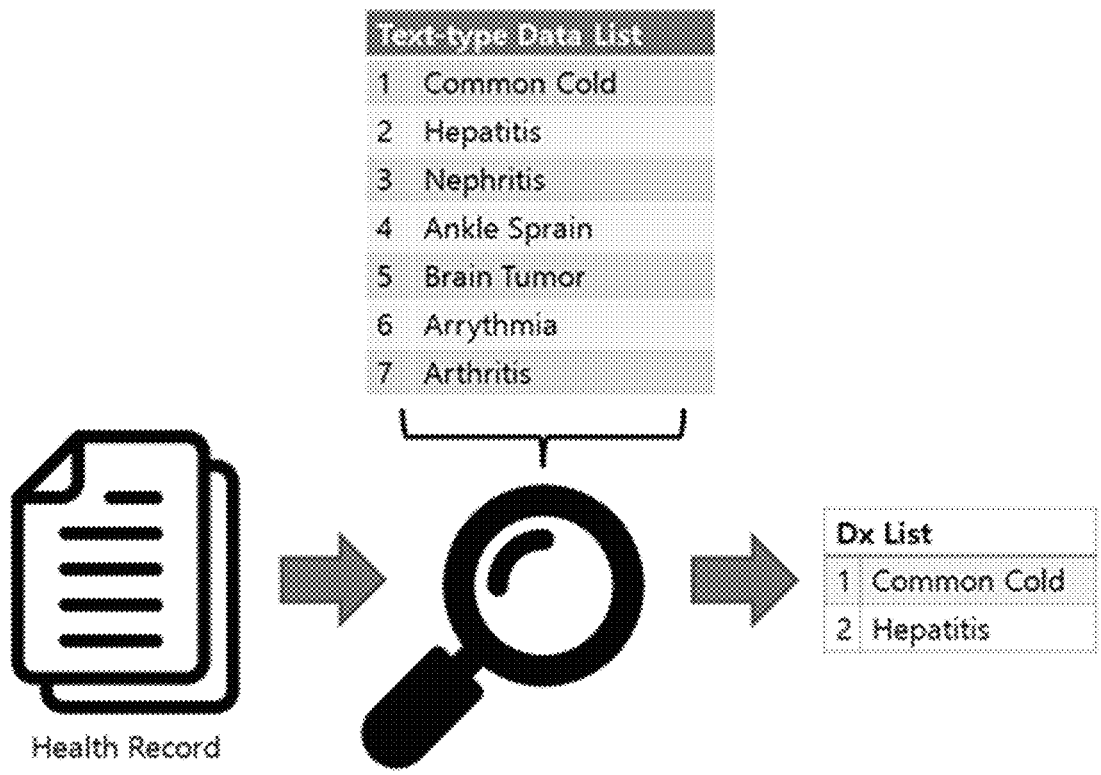
FIG. 17 is an embodiment illustrating a method of extracting data by the data extraction module (100) when the text-type data (120) for generating the image-type data (210) is stored in the medical data (110) separately for each "diagnosis name" or each "symptom".
FIG. 18 is an embodiment illustrating a method of extracting data to the text-type data (120) by the data extraction module (100) when the text-type data (120) for generating the image-type data (210) is free-text data which is not organized into separate items, or unstandardized strings or binary large object (BLOB)-type data in a database.

In addition, when the text-type data 120 is free-text data that is not organized into separate items, unstandardized character strings, or data in the form of binary large object (BLOB) data in a database, as illustrated in FIG. 18, a list of the text-type data 120 may be specified for the required items, and required values may be extracted. The data extraction module 100 is configured to collect information from data scattered in various hospitals and distributed to external servers.

Next, the visualization module 200 generates the text-type data 120 collected by the data extraction module 100 as visualization data. More specifically, the acquired text-type data 120 is converted into image-type data 210. At this time, the image-type data 210 is a predetermined 3D model, and may be generated by combining one or more medical information models 212 with a basic model 211 which is a 3D model.

Figure 2:
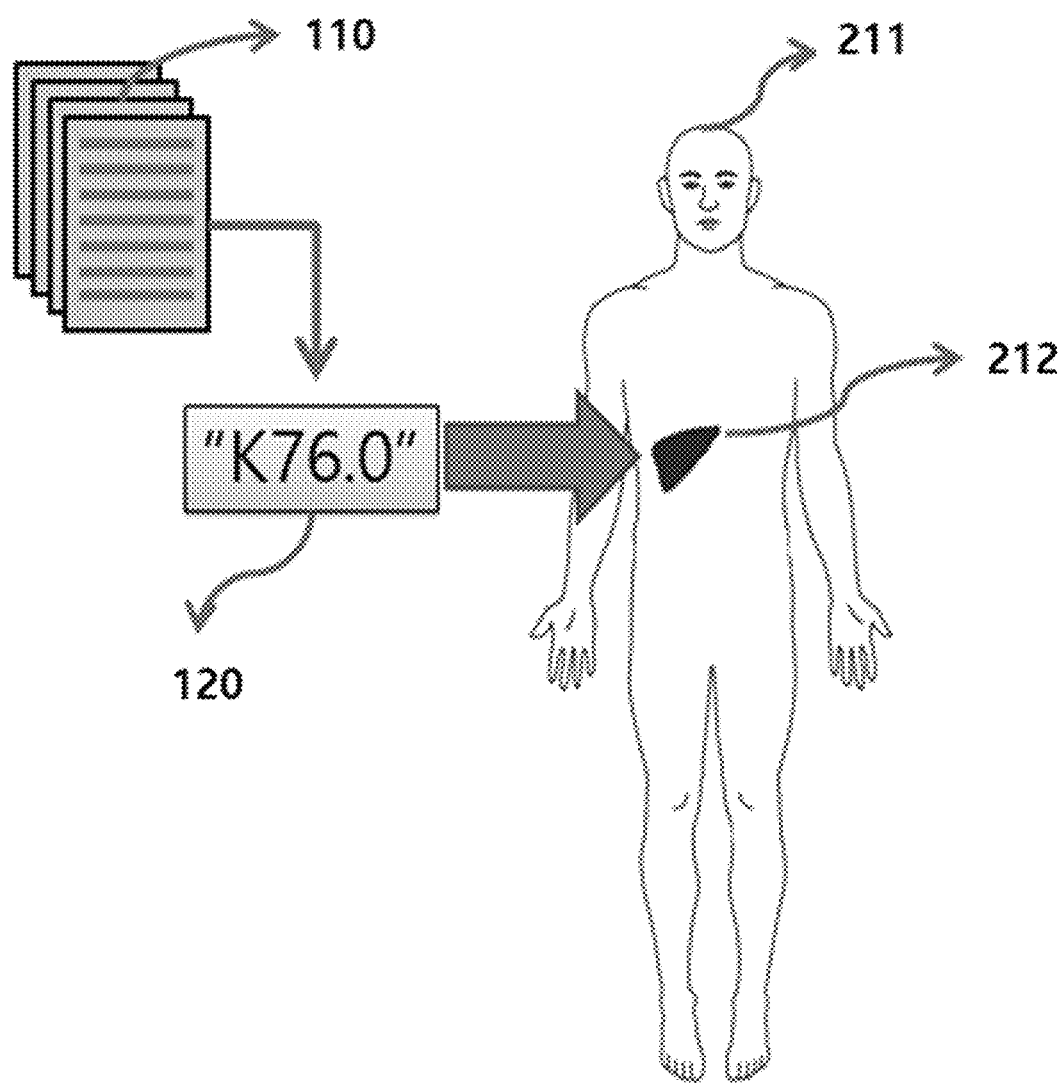
FIG. 2 is a schematic diagram schematically illustrating a configuration of converting medical data (110) into a 2D medical information model (212) in a configuration of a data extraction module (100).
Figure 3:
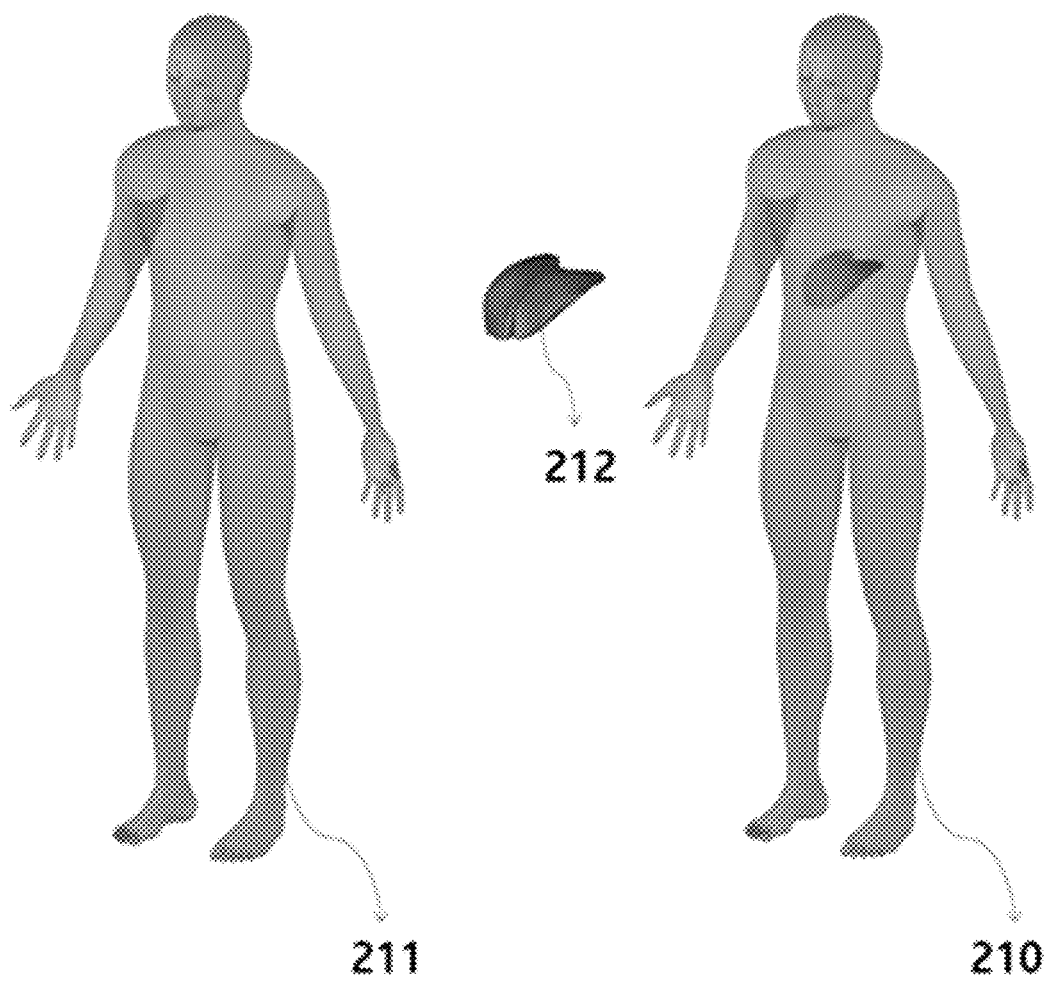
FIG. 3 is a schematic diagram schematically illustrating a configuration of converting medical data (110) into a 3D medical information model (212) in the configuration of the data extraction module (100).

As illustrated in FIGS. 2 and 3, the information representing the medical data 110 is expressed as the image-type data 210, which is an image including the medical data 110. The image-type data 210 includes the medical information model 212 representing the text-type data 120 acquired from the medical data 110 and an image (basic model 211) which is an image expressing the human body. The medical information model 212 may be expressed in more detail by dots, lines, areas, volumes, or various shapes or combinations thereof, and may be expressed as a 2D model as well as a 3D model.

Figure 4:
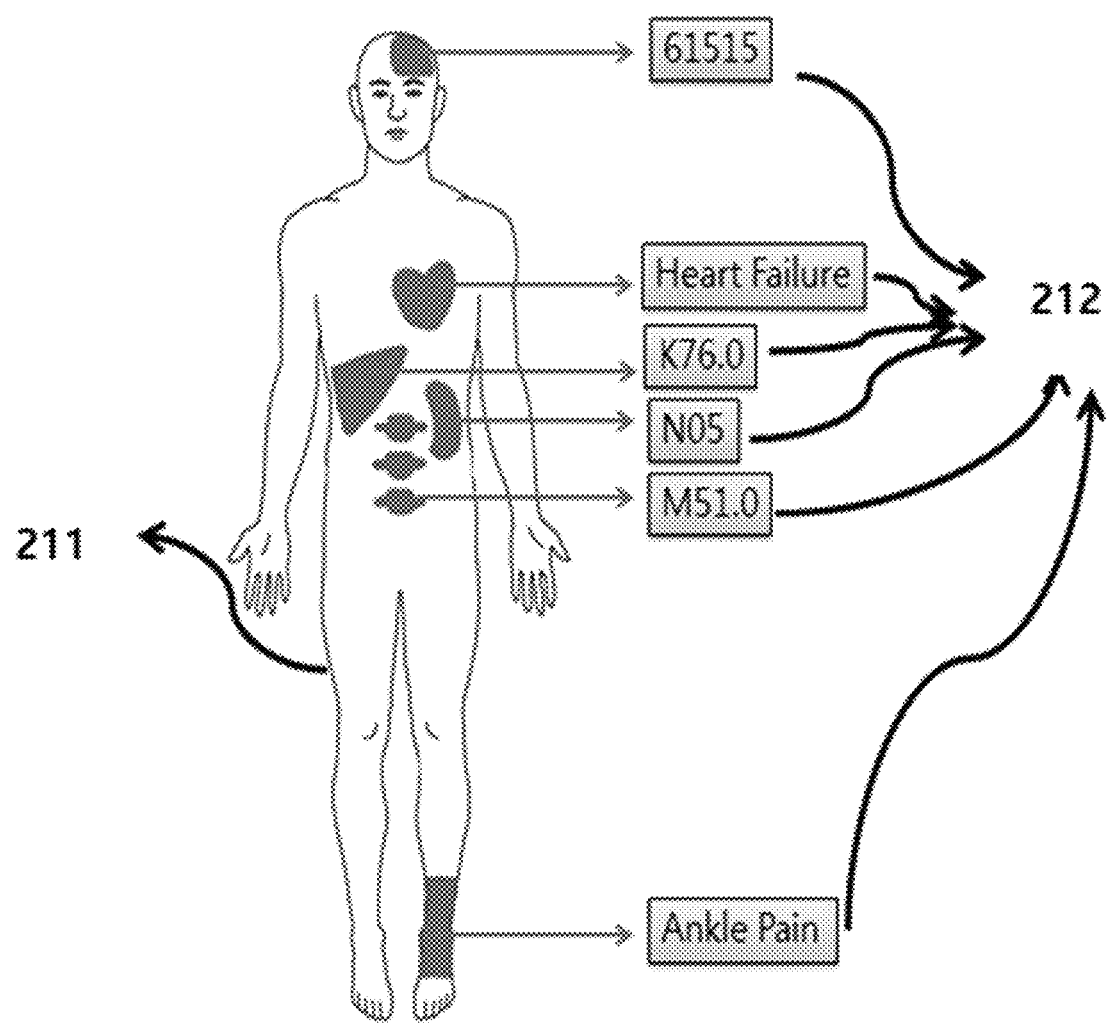
FIG. 4 is a schematic diagram schematically illustrating a configuration of adding the medical information model (212) in a basic model (211) in the configuration of the data extraction module (100).
Figure 5:
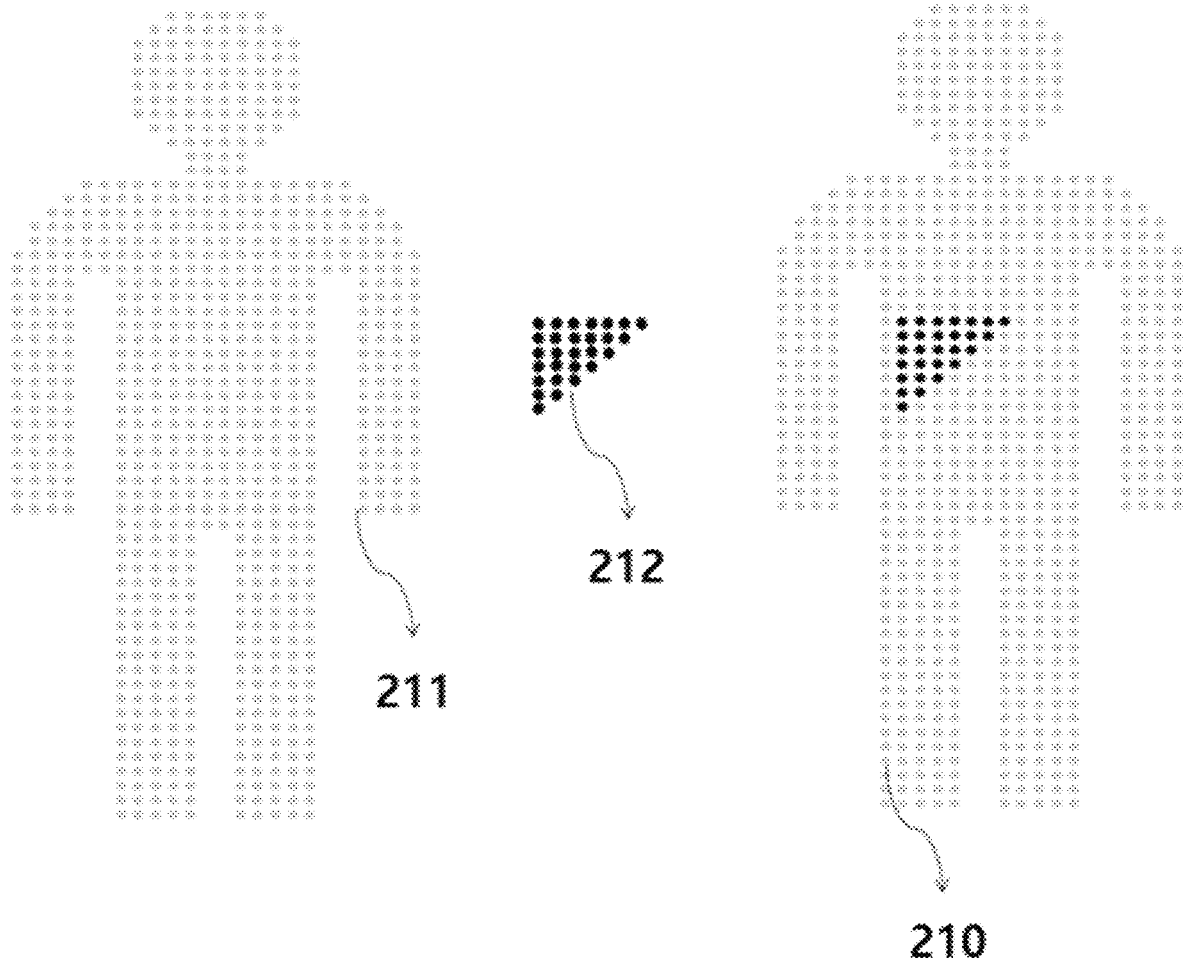
FIG. 5 is another schematic diagram schematically illustrating a configuration of adding the medical information model (212) in the basic model (211) in the configuration of the data extraction module (100).

As illustrated in FIG. 4, the basic model 211 may include the plurality of medical information models 212 to provide the image-type data 210. The plurality of medical information models 212 that have been previously prepared and stored are referred to the text-type data 120 extracted from the medical data 110 and used as a medical information model 212 of a certain patient.

The basic model 211 may also be an empty space in which no picture is drawn, and at this time, the visualization module 200 may express the medical information model 212 in the empty space. Equipment learning may be performed even if the basic model is the empty space. In addition, the image-type data 210 may be a whole body and may represent only some systems of the human body, such as a digestive system or a respiratory system, or may represent only a certain area of the body, such as a left leg or a head.

The medical information model 212 may be a model of entire organ or part of an organ. For example, in the case of a tumor occurring from the liver, the entire liver organ may be expressed as the medical information model 212 or a portion where the tumor occurs, that is, a segment (e.g., posterior lateral segment) that is a part of the liver. Alternatively, the medical information model 212 may also be expressed as a shape itself in which the tumor occurs.

In addition, the medical information model 212 may be added or drawn directly to be imaged by a user without being extracted from the medical data 110. In the medical information model 212, a patient or a medical person may directly draw a painful spot, or express a site with a spot, an itchy site, a site where a blood pressure is checked, a site where a nail is cut, and a site to be injected. For example, when the patient has a fatty liver, the medical person may directly draw the basic model 211 in the background without recording the medical data 110. Alternatively, as illustrated in FIG. 4, the medical person or the patient may select one of the medical information models 212 prepared and stored in advance to express a disease condition of a patient.

The visualization module 200 varies the color, brightness, or transparency of the image according to the name of the disease, the severity of the disease, the chronicity, and the degree of malignancy. The visualization module 200 may determine the color of the image by selecting or combining any one or more of red, green, and blue colors. In one embodiment, the patient may have a paralysis of the tibialis anterior muscle. If the muscle strength of the corresponding muscle is 20% of the normal, an R value representing the red color among RGB channels which are colors expressing the muscle strength may represent the muscle strength with 20% of the maximum value, and if the maximum value of the red channel is 255, the R value may be expressed as 255*0.2=50.5. On the other hand, the function of the kidney may be confirmed by an estimated glomerular filtration rate (eGFR) as one of the blood tests, and may be represented as 255 if the eGFR is 100 and 255/2 if the eGFR is 50 in conjunction with a G value representing the green value to the eGFR value. If the eGFR is 0, the G value may be represented as 0. That is, the patient's condition may be represented by changing and expressing the attributes of the image by a function of using a result value of the blood test as a factor. As such, the color may be defined as a value determined by a function of using clinical data as a factor.

Figure 6:
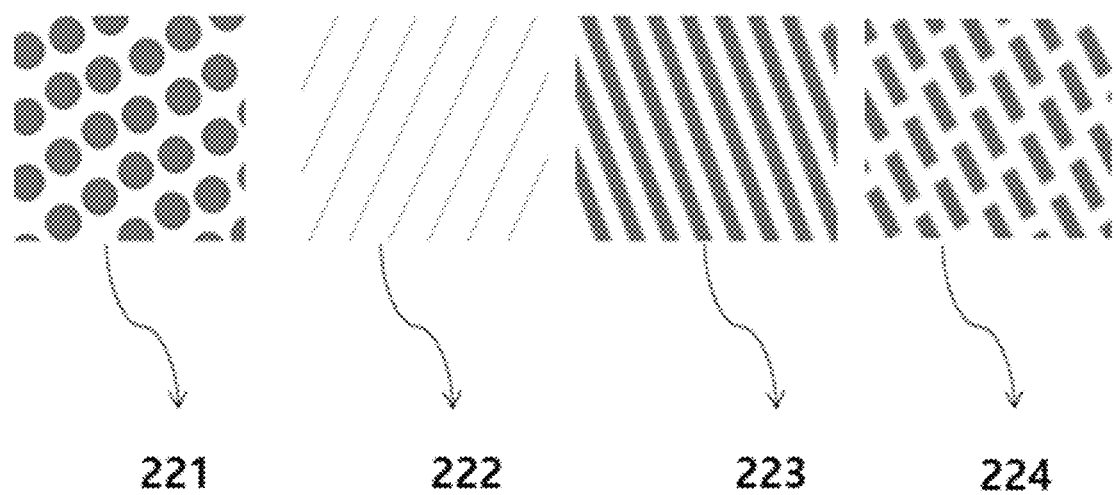
FIG. 6 is an embodiment illustrating a round pattern (211), a thin diagonal pattern (222), a thick diagonal pattern (223), and a dotted diagonal pattern (224) in a configuration of a visualization module (200).

As illustrated in FIG. 6, the image-type data 210 may be completed in the medical information model 212 by adding a texture 220 to the basic model 211 in addition to general image attributes such as color, brightness, and transparency.

In addition, the visualization module 200 may express the texture 220 in the medical information model 212 according to a name of the disease, a medical term code, the chronicity, severity, and the degree of malignancy. For example, as illustrated in FIG. 6, the stenosis may be expressed by a round pattern 211, the squamous cell carcinoma may be expressed by a thin diagonal pattern 222, the hemangioma may be expressed by a thick diagonal pattern 223, and the paralysis may be expressed by a dotted diagonal pattern 224. The patterns presented herein represent a few of examples of the texture 220, and the texture 220 is not limited thereto and may be prepared by using a man-made figure, an icon representing a disease, or the like. In addition, the image-type data 210 may be expressed by applying various types of clinical data as well as the shape of the pattern.

Figure 7:
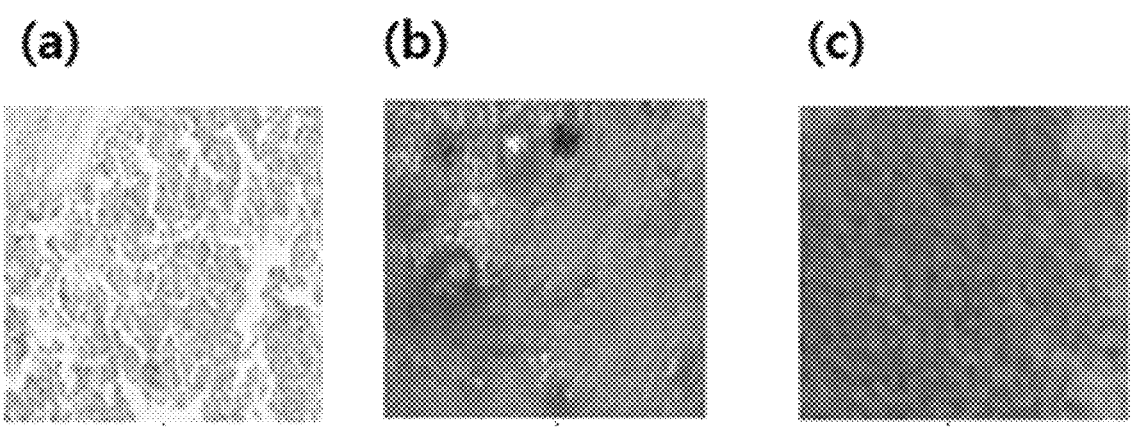
FIG. 7 is a photograph illustrating an embodiment capable of using images extracted directly from a medical image, anatomical pathology findings, skin disease photographs, etc. as a texture (220).
Figure 8:
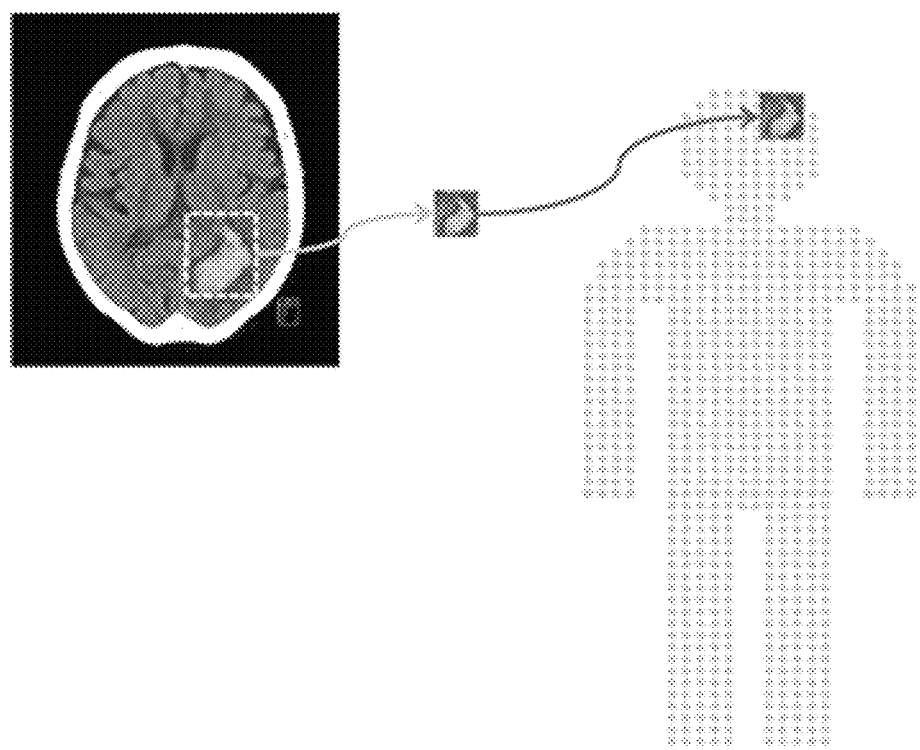
FIG. 8 illustrates an embodiment of the image extracted directly from the medical image and is a diagram illustrating a case where a part of a CT image is taken to generate a texture (220) for a medical information model (212) of a patient with brain hemorrhage.

In addition, an image extracted from a medical image, a photograph or image showing an anatomical pathology finding, an image to be photographed or extracted such as a skin disease photograph, and the like may be provided so as to be directly converted into the texture 220. That is, all medical images may be applied to the medical information model 212. For example, in FIG. 7A, microscopic tissue findings may be used as the texture 220, and typical pathological findings that may well express the patient's condition or a photograph of the corresponding patient may be taken directly. FIG. 7B is an image of photographing a skin lesion, and the image may be used as the texture 220 in a corresponding region and may also be a photograph of directly photographing a patient's skin. FIG. 7C is a part of an image photographed by an MRI. In addition, FIG. 8 illustrates a case in which a part of the CT image is taken to make the texture 220 of a patient with brain hemorrhage. As such, more various clinical data may be imaged, which may be used as equipment learning data.

Figure 9:
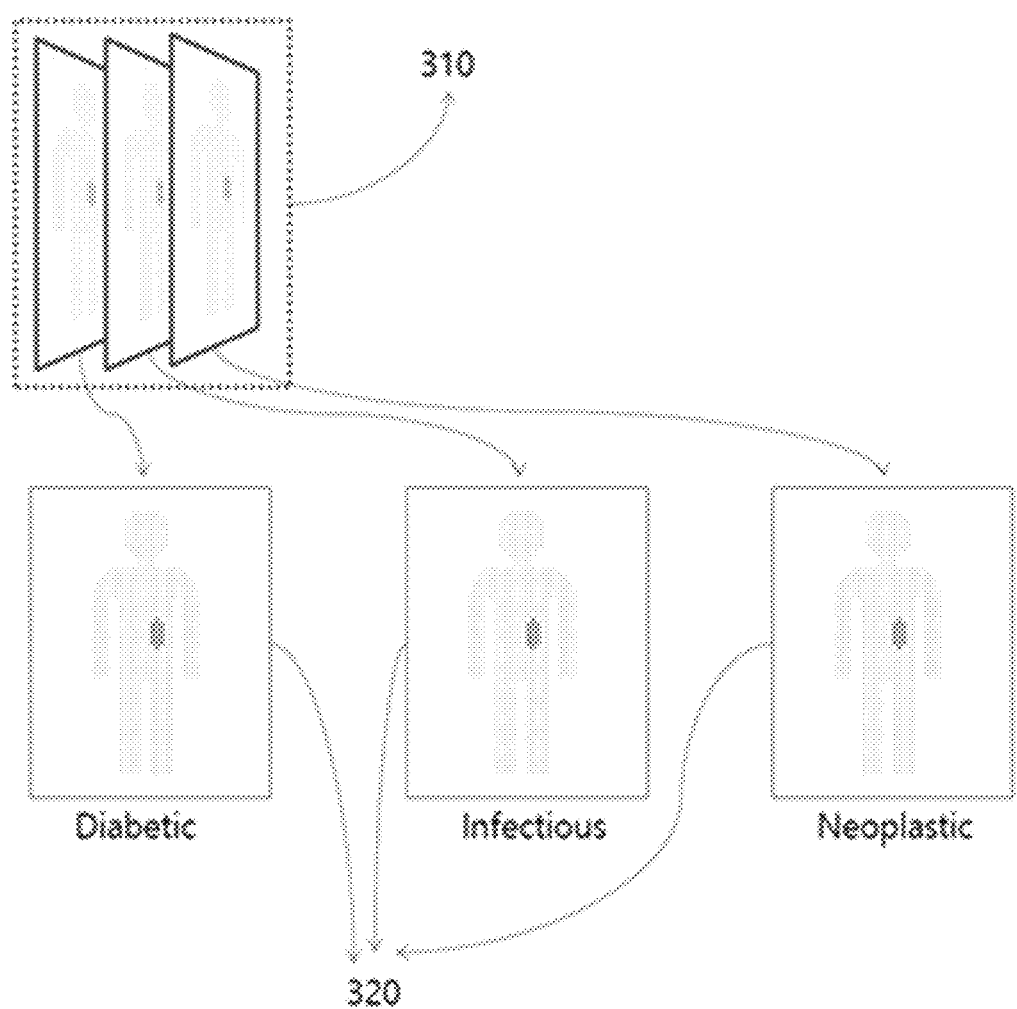
FIG. 9 is a diagram showing using one or more layers according to characteristics of the medical data (110) to further expand expression of information of the visualization module (200).

In FIG. 9, the visualization module 200 is characterized to use one or more layers according to the characteristics of the medical data 110 to further expand expression of information. When there are many concurrent diseases in the kidney, various disease conditions may be expressed in multiple layers which represent disease categories. As illustrated in FIG. 9, diabetic kidney disease, infectious kidney disease, and neoplastic kidney disease may be simultaneously expressed and represented.

Figure 13:
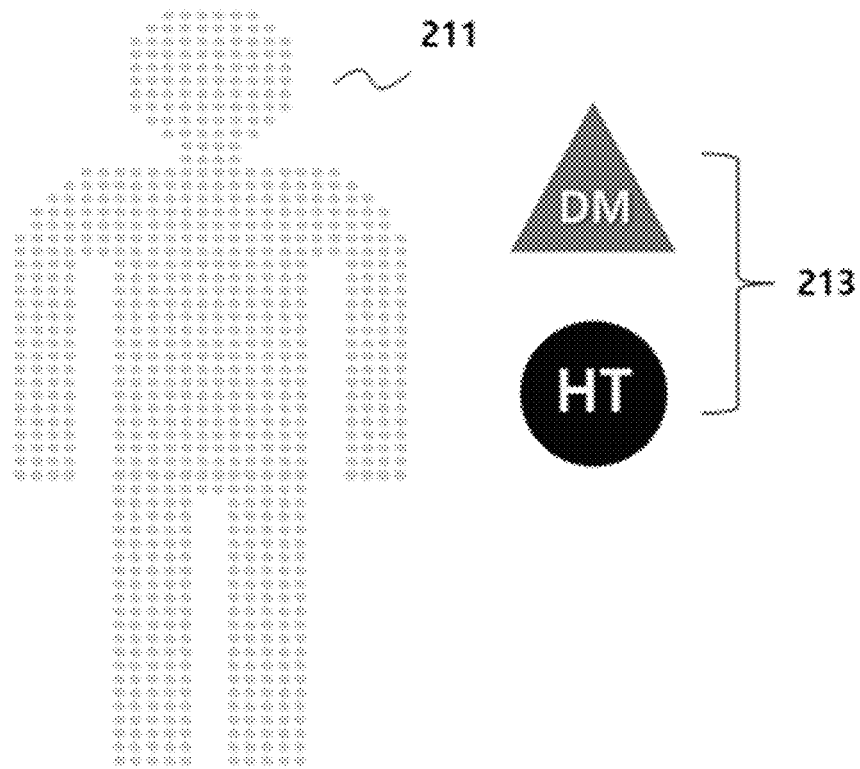
FIG. 13 is a diagram for describing the medical information model (212) that further expresses diseases or symptoms which are not able to be anatomically expressed inside and outside the body in the basic model (211).

The visualization module 200 may further include the medical information model 212 that further expresses patient's diseases or symptoms which are not able to be anatomically expressed inside and outside the body shown in the basic model 211. Based on the basic model 211 expressing the human body, there may be more medical information that cannot be expressed by the medical information model 212. For example, the medical information is high blood pressure and diabetes. Of course, in the case of diabetes, the malfunction of the pancreas may be the cause, but when a relationship with the pancreas cannot be confirmed, it may be difficult to express information due to this pancrease condition. FIG. 13 illustrates an embodiment of the medical information model 212 that additionally shows a model of diabetes and hypertension outside the body to compensate for this.

Figure 19:
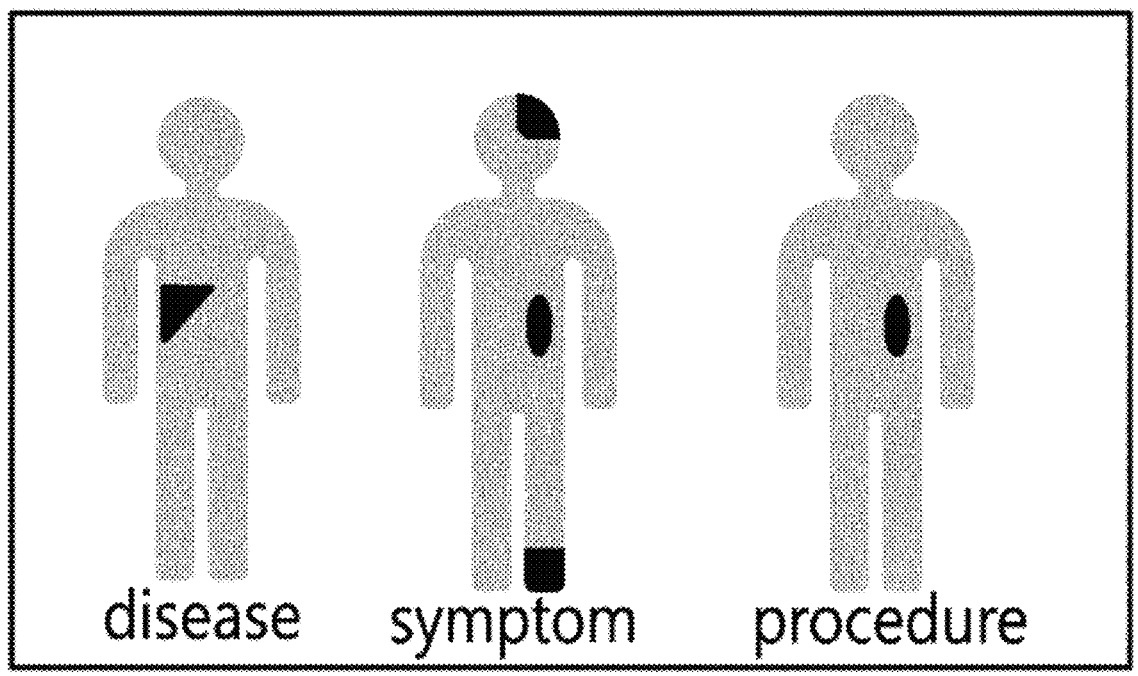
FIG. 19 is an embodiment illustrating a form of visualizing data in one or more basic models (211) by the visualization module (200).

FIG. 19 illustrates a form of visualizing data on a plurality of basic models 211 by the visualization module 200, and illustrates an example of visualizing information classified by disease, symptom, and procedure in each of the basic models 211 as the medical information model 212. In a manner in which data is separately recorded according to the classification of the text-type data 120 in the plurality of basic models 211, in this case, there are advantages of managing the medical data 110 by type as needed and of being able to describe more accurately the medical data 110.

Next, the pre-processing module 300 generates an input data set 310 for executing equipment learning based on the visualization data. The pre-processing module 300 generates the input data set 310 by processing the visualization data in a required form. The pre-processing module 300 may generate the input data set 310 by normalizing various types of image-type data 210 having various formats.

In the pre-processing of the data, when the image generated from the visualization data is a 2D image, data defined as one image in RGBA channels at a resolution of 50×50 may be defined as one input data set 310. Alternatively, in the case of 3D data, an image created by applying the RGBA channels to each voxel at a resolution of 50×50×50 may be defined as one input data set 310.

Meanwhile, the pre-processing module 300 may create a data set reflecting a change in data according to a change in time and provide the created data set as a learning material. That is, multiple image-type data 210 generated by the visualization module 200 may be generated as needed. For example, first data was generated from information on hospitals visited at the age of 20, second data was generated from information on hospitals visited at the age of 30, and third data was generated from information on hospitals visited at the age of 40, so that a total of three data were generated. The data made as temporal data or videos using the three data to reflect the passage of time may also be provided as the input data set 310. That is, the pre-processing module 300 may learn a trend of the data according to a change in time point by combining materials prepared at various time points.

Figure 10:
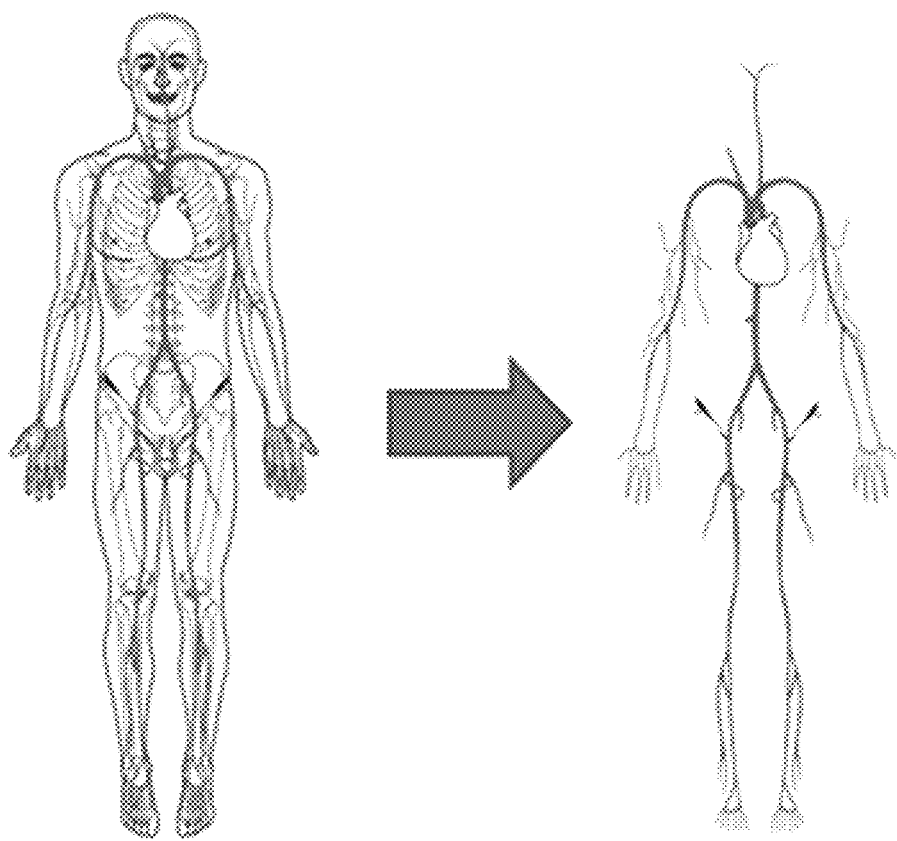
FIG. 10 is an embodiment of generating an input data set (310) by processing only a vascular system medical information model by a pre-processing module (300) among the image-type data (210) generated by the visualization module (200).
Figure 11:
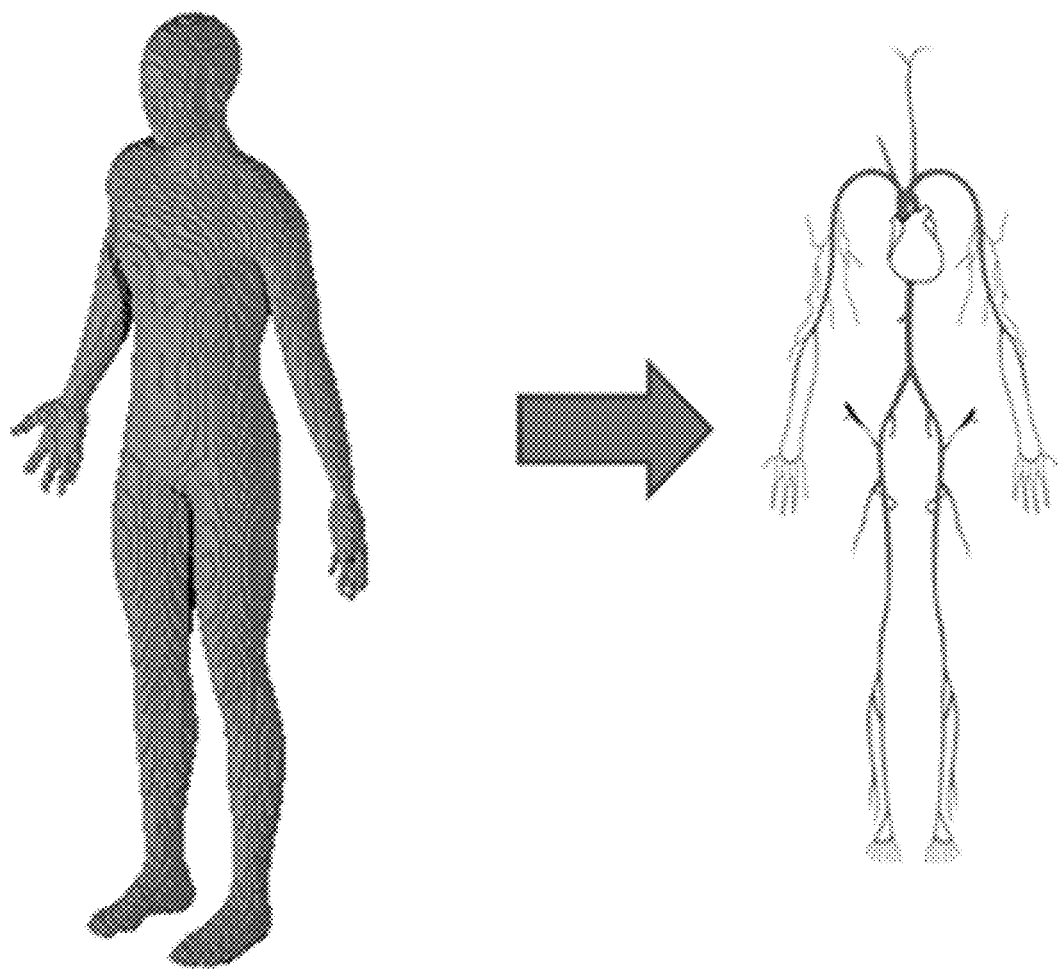
FIG. 11 illustrates an embodiment of generating the input data set (310) with the 2D-converted data among the 3D-expressed image-type data (210) by the pre-processing module (300).
Figure 12:
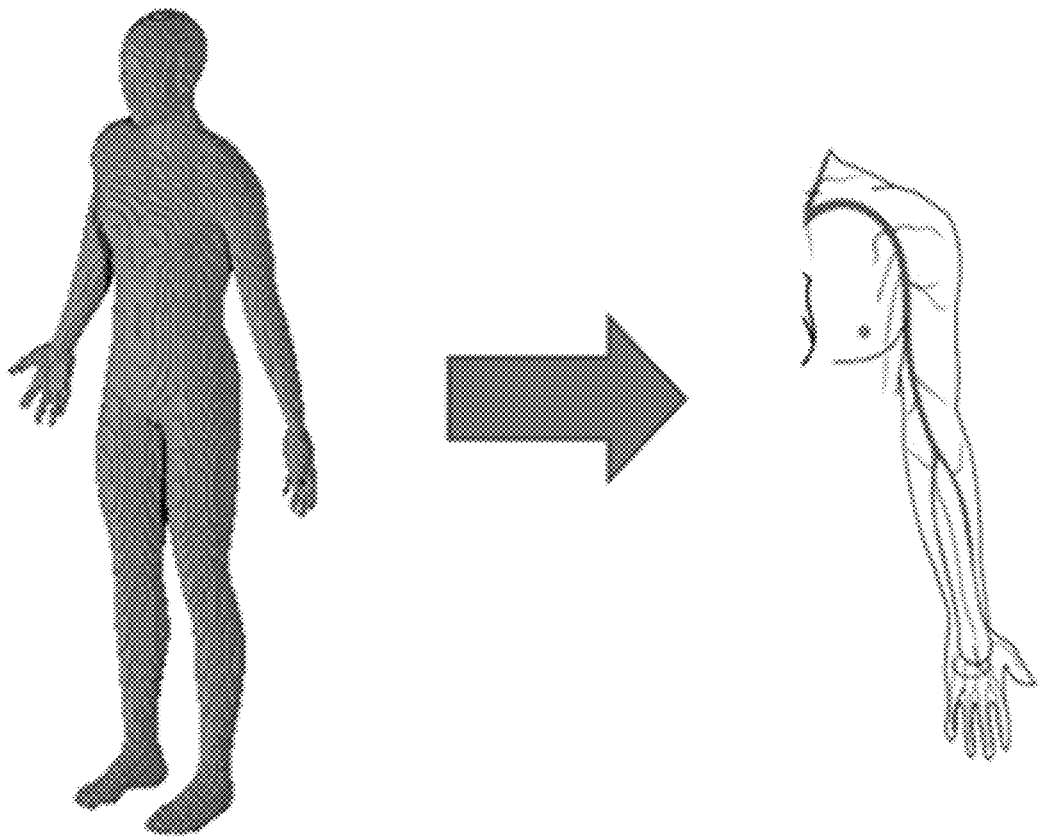
FIG. 12 illustrates an embodiment of generating the input data set (310) with only a left shoulder and an upper arm while being converted into the 2D data among the 3D-expressed image-type data (210) by the pre-processing module (300).

As illustrated in FIGS. 10 to 12, the pre-processing module 300 may generate the input data set 310 by normalizing various types of image-type data 210 having various formats. The normalized input data set 310 is provided to the learning module 400.

FIG. 10 is an embodiment of generating the input data set 310 by processing only a vascular system medical information model by the pre-processing module 300 among the image-type data 210 generated by the visualization module 200. The pre-processing module 300 may convert the input data set 310 by selecting only a portion of the image-type data 210.

FIG. 11 illustrates an embodiment of generating the input data set 310 with the 2D-converted data among the 3D-expressed image-type data 210 by the pre-processing module 300.

FIG. 12 illustrates an embodiment of generating the input data set 310 with only a left shoulder and an upper arm while being converted into the 2D image among the 3D-expressed image-type data 210 by the pre-processing module 300.

Next, the learning module 400 executes equipment learning on the input data set 310 generated by the pre-processing module 300. The learning module 400 may include an algorithm that may be classified as equipment learning, such as a support vector equipment, a convolutional neural network, and a generative adversarial neural network.

Next, the prediction module 500 predicts data when the new image-type data 210 is input based on the results learned in the learning module 400.

Figure 14:
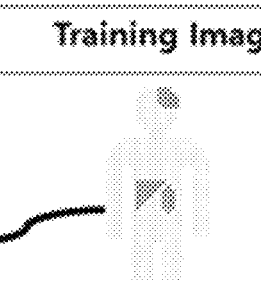
FIG. 14 illustrates an embodiment of performing equipment learning by using a learning module (400).

FIG. 14 illustrates an embodiment of learning life extension by using the learning module 500. In FIG. 14, a training image represents the input data set 310 input from the pre-processing module 300. The first image is a condition in which a person cannot be moved well with a lesion in the left brain, diseases in the liver and the kidney, and a disease in the leg. The second image is an image with diseases of the liver and the kidney, and the third image is an image with diseases in only the legs. For each image, life expectancies of 3, 15, and 30 years were given as target values.

Figure 15:
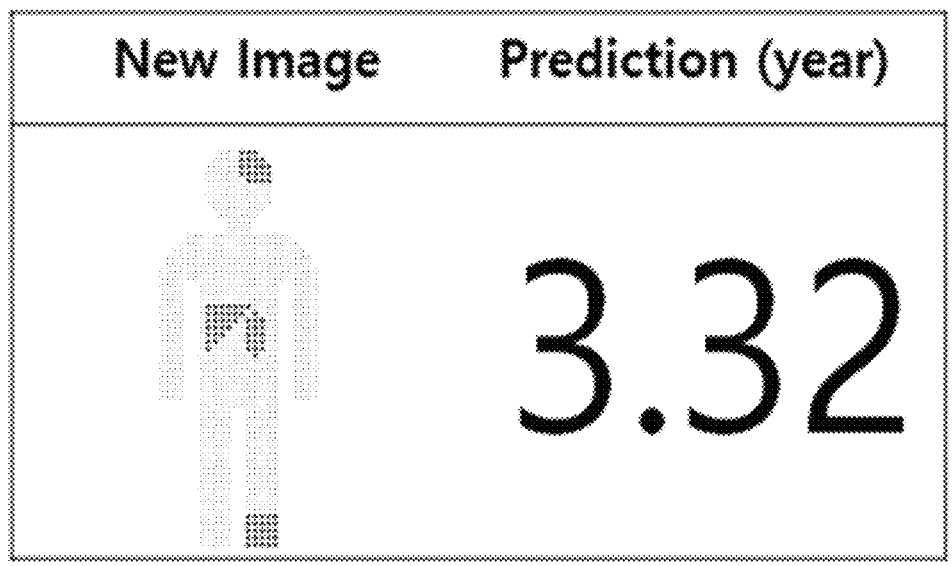
FIG. 15 is an embodiment of presenting a prediction value by inputting new image-type data (210) after learning by the learning module (400).

FIG. 15 is an embodiment of presenting a prediction value by receiving new image-type data 210 after learning by the learning module 400. In the prediction module 500, it is possible to present a prediction value for a life expectancy, such as 3.32 years.

By the technical solution, according to the present invention, it is possible to provide a medical AI learning system capable of avoiding disadvantages of existing text-type data and improving performance of AI by converting medical information expressed in texts into images and using the converted images for AI learning.

Further, according to the present invention, it is possible to normalize text-type materials which have different lengths while having ambiguous meanings.

Further, it is possible to provide medical information having a richer meaning by converting text-type data into image-type data.

Further, it is possible to implement a medical AI system capable of predicting precise and accurate diseases.

As described above, it will be understand to those skilled in the art that a technical configuration of the present invention can be easily executed in other detailed forms without changing the technical spirit or an essential feature thereof.

Therefore, the embodiments described as above are exemplary in all aspects and should be understood as not being restrictive and the scope of the present disclosure is represented by claims to be described below rather than the detailed description, and it is to be interpreted that the meaning and scope of the claims and all the changes or modified forms derived from the equivalents thereof come within the scope of the present invention.

EXPLANATION OF REFERENCE NUMERALS AND SYMBOLS

1. Medical equipment learning system
100. Data extraction module
110. Medical data
120. Text-type data
200. Visualization module
210. Image-type data
211. Basic model
212. Medical information model
220. Texture
221. Round pattern
222. Thin diagonal pattern
223. Thick diagonal pattern
224. Dotted diagonal pattern
300. Pre-processing module
310. Input data set
400. Learning module
500. Prediction module
600. Storage module

The invention claimed is:

1. A medical machine learning system comprising:
a data extraction module configured to collect and then extract text-type data from medical data;
a visualization module configured to generate image-type data as visualization data by retrieving a previously stored medical information model which references the text-type data extracted by the data extraction module;
a pre-processing module configured to generate an input data set to execute machine learning based on the visualization data;
a learning module configured to execute machine learning in the input data set generated by the pre-processing module by using an algorithm including a support vector equipment, a convolutional neural network, or a generative adversarial neural network;
a prediction module configured to predict a disease when new image-type data is input based on a comparison with a result of the machine learning in the input data set in the learning module; and
a storage module provided to store and check data of each module,
wherein the data extraction module, the visualization module, the pre-processing module, the learning module, the prediction module, and the storage module are each implemented via at least one processor.

2. The medical machine learning system of claim 1, wherein the image-type data generated by the visualization module is a predetermined 2D or 3D model.

3. The medical machine learning system of claim 1, wherein the data extraction module collects the medical data by receiving materials from any one or more of a portable file, a hospital, a cloud server, and a personal device.

4. The medical machine learning system of claim 1, wherein the visualization module expresses a name of a disease, a severity of the disease, a chronicity, a degree of malignancy, various test results, functional test results, and data results extracted from a machine by any one or more of colors, brightness or transparency, patterns, and textures of the visualization data.

5. The medical machine learning system of claim 1, wherein the visualization module uses an image extracted from a medical image or an anatomical pathology photograph as a texture.

6. The medical machine learning system of claim 1, wherein the visualization module uses one or more layers according to characteristics of the medical data.

7. The medical machine learning system of claim 1, wherein the visualization module generates the image-type data by combining one or more medical information models.

8. The medical machine learning system of claim 1, wherein the pre-processing module generates the input data set by normalizing various types of image-type data having different standards.

9. The medical machine learning system of claim 1, wherein the visualization module further includes a medical information model expressing medical information which is not anatomically related inside and outside a body in a basic model.

10. The medical machine learning system of claim 1, wherein the pre-processing module creates temporal data by combining several image-type data having different creation time points and generates the input data set according to a change in time.

11. The medical machine learning system of claim 1, wherein the pre-processing module forms the input data set by selecting only a portion of an image-type data area.

12. The medical machine learning system of claim 1, wherein the pre-processing module generates the input data set 2-dimensionally converted from the image-type data expressed 3-dimensionally.

* * * * *